(12) United States Patent
Li et al.

(10) Patent No.: US 6,593,394 B1
(45) Date of Patent: Jul. 15, 2003

(54) BIOACTIVE AND OSTEOPOROTIC BONE CEMENT

(75) Inventors: Yiwen Li, Quarry Bay (HK); Weijia William Lu, South Horizons (HK); Man Chee Kenneth Cheung, Hong Kong Garden (HK); Dip Kei Keith Luk, Scenic Villa (HK); Chi Yan John Leong, Tam Gardens (HK)

(73) Assignee: Prosperous Kingdom Limited, Hong Kong (HK)

( * ) Notice: Subject to any disclaimer, the term of this patent is extended or adjusted under 35 U.S.C. 154(b) by 0 days.

(21) Appl. No.: 09/710,536

(22) Filed: Nov. 9, 2000

Related U.S. Application Data (60) Provisional application No. 60/174,204, filed on Jan. 3, 2000.

(51) Int. Cl.[7] .......................... A61L 27/12; A61L 27/16; A61K 6/033; A61K 6/083
(52) U.S. Cl. ...................... 523/113; 523/114; 523/115; 523/116; 523/118; 424/422
(58) Field of Search ................. 523/118, 113, 523/114, 116, 115; 424/422

(56) References Cited

U.S. PATENT DOCUMENTS

| | | | | |
|---|---|---|---|---|
| 4,604,097 A | * | 8/1986 | Graves | 623/11 |
| 4,871,786 A | * | 10/1989 | Aasen et al. | 523/113 |
| 4,963,151 A | | 10/1990 | Ducheyne et al. | |
| 5,059,209 A | * | 10/1991 | Jones | 623/23 |
| 5,328,262 A | | 7/1994 | Lidgren et al. | |
| 5,795,922 A | | 8/1998 | Demian et al. | |
| 5,849,865 A | * | 12/1998 | Cheng | 530/317 |
| 5,866,155 A | * | 2/1999 | Laurencin et al. | 424/425 |
| 5,876,460 A | * | 3/1999 | Bloebaum | 623/18 |
| 5,914,356 A | * | 6/1999 | Erbe | 523/114 |
| 5,951,836 A | * | 9/1999 | McAleer et al. | |
| 5,955,514 A | * | 9/1999 | Huang et al. | 523/118 |
| 5,976,788 A | * | 11/1999 | Russo | 435/6 |
| 6,221,931 B1 | * | 4/2001 | Sakuma et al. | |
| 6,270,751 B1 | * | 8/2001 | Resler | |

FOREIGN PATENT DOCUMENTS

| | | |
|---|---|---|
| EP | 0411208 | 2/1991 |
| JP | 59217666 | 7/1984 |
| JP | 63305874 | 12/1988 |
| WO | 9316738 | 9/1993 |

OTHER PUBLICATIONS

Ratier, A. et al., "Setting characteristics and mechanical behaviour of a calcium phosphate bone cement containing tetracycline", Biomaterials 22 (2001) pp. 897–901.
Eni–Olutu, D.O. et al., "The Use of Handheld Cement Sample as a Guide to the Setting of In Situ Cement Mantle", The Journal of Arthropl asty, vol. 16, No. 3, 2001, pp. 376–378.
Tawfik, Hatem A. et al., "Orbital Implants in Postenucleation Retinoblastoma", Ophthalmology, vol. 108, No. 4, Apr. 2001, pp. 639–640.
Torrado, Susana et al., "Gentamicin bone cements: characterisation and release (in vitro and in vivo assays)", International Journal of Pharmaceutics 217 (2001), pp. 57–69.
Wilkinson, J.M. et al., "Measuring bone mineral density of the pelvis and proximal femur after total hip arthroplasty", The Journal of Bone and Joint Surgery, vol. 83–B, No. 2, Mar. 2001, pp. 283–288.
Wimhurst, J.A. et al., "Inflammatory responses of human primary macrophages to particulate bone cements in vitro", The Journal of Bone and Joint Surgery, vol. 83–B, No. 2, Mar. 2001, pp. 278–282.
Geeter, K. De, et al., "Metastatic Fractures of the Tibia", Acta Orthopaedica Belgica, vol. 67—1 (2001), pp. 54–59.
Kokubo, Tadashi, et al., Bioactive Bone Cement Based on CaO–SiO2–P2O5 Glass, Communications of the American Ceramic Society, vol. 74, No. 7, Jul. 1991, pp. 1739–1741.

* cited by examiner

Primary Examiner—Tae H. Yoon
(74) Attorney, Agent, or Firm—Jones Day (57) ABSTRACT

A composition for use as a bioactive bone cement having a powder component including strontium-containing hydroxy apatite and formulated to create a settable fluid substance when mixed with a liquid component. The liquid component includes a Bisphenol A diglycidylether dimethacrylate resin which when mixed with the powder component creates a bioactive bone cement. The bioactive bone cement can alternatively be in the form of a two paste component system in which a first paste component including strontium-containing hydroxy apatite, Bisphenol A diglycidylether dimethacrylate resin and a polymerization initiator is formulated to create a settable paste substance when mixed with a second paste component. The second paste component includes strontium-containing hydroxy apatite, Bisphenol A diglycidylether dimethacrylate resin, and a polymerization accelerator which when mixed together with the first paste component creates a bioactive bone cement.

10 Claims, 7 Drawing Sheets

BIOACTIVE AND OSTEOPOROTIC BONE CEMENT

This application claims the benefit of Provisional Application 60/174,204 filed on Jan. 3, 2000.

FIELD OF THE INVENTION

The present invention relates to bone cement compositions used in the bonding or fixing of implant materials, as well as in the strengthening of damaged natural bone. The present invention further relates to bone cement compositions having bioactive properties.

BACKGROUND OF THE INVENTION

Bone cement compositions are useful in the bonding or fixing of an implant material, as well as in the strengthening of damaged natural bone. Such applications are particularly useful in the areas of orthopedics, dentistry and related medical disciplines. The field of orthopedics deals with bone defects due to fracture, bone tumors, and other diseases of the bone. Treatment may require surgical resection of all, or part, of a bone. In dentistry applications, a defected jawbone may result from extraction of a tooth, cancer or other diseases. An implant material is useful in repairing or reconstructing the bone remaining after the resection of such bone defects. Implant materials used during such procedures are frequently comprised of metal, ceramics and polymers.

It is advantageous for the implant material to be able to quickly adapt in order to embed and fix in the repaired site. To facilitate this, the implant material must either be ground or worked into a shape adapted to the repair site. However, it is difficult to perform this work with the high precision necessary. Because of the limitations of implant materials, bone cement is often used with the implant material in order to bond and affix the implant to the remaining, living bone. For example, polymethyl methacrylate (PMMA) has been widely used with hardware instrumentation in orthopedics.

Although conventional PMMA bone cement has been used in orthopedic surgery for over 40 years, it is far from ideal because 1) it does not encourage bone in-growth, 2) it is a weaker implement than bone cortex, and 3) it has a high exotherm and monomer toxicity. Research, focusing on bioactive bone cements, has been ongoing to modify or replace conventional PMMA bone cement to eliminate or reduce these limitations.

Sogal et al. modified PMMA by adding hydroxy apatite (HA) powder. It is also known to add bone particle and growth hormone to PMMA. Japanese Patent Publication No. 42384/1979 discloses a biocement comprised of a combination of polymethyl methacrylate (PMMA) and $K_2O$—$Na_2$—$CaO$—$MgO$—$SiO_2$—$P_2O_5$ crystallized glass powder.

Although some improvement has been made to conventional PMMA, fundamental problems remain with the methyl methacrylate (MMA)/PMMA system. Brown et al. developed a new type of bioactive calcium phosphate cement originally used in dentistry in the 1980s. Although this bioactive cement showed good bioactivity with bone, its weak mechanical properties made it unsuitable for use in repairing weight-bearing bones. In addition, the long setting time of this cement made it impractical for use in many applications.

Recently, a number of alternatives to the basic MMA/PMMA system have been explored, such as bioactive filler-Bis-GMA systems. Japanese Patent Prepublication No. 503148/1987 and U.S. Pat. No. 5,527,386 disclose this type of bioactive cement, comprised of a combination of 2,2-bis[4-(3-methacryloxy-2-hydroxy propoxy) phenyl] propane (Bis-GMA) base monomer and apatite powder with bioglass powder added as an optional component. Another example of developing bioactive cement systems is British HA reinforced poly (ethyl methacrylate)/n-butyl methacrylate (PEMA-nBMA). However, these types of bioactive bone cements are not yet satisfactory with respect to bonding to living bone, bond strength, mechanical strength, and chemical stability of the hardened cement core. Bis-GMA cement is especially limited in that it displays poor handling properties and potential increases in stresses in vivo due to its high modulus. However, Bis-GMA cement does display significant bioactivity. PEMA-nBMA is especially limited in that it has an unacceptably low creep resistance when unfilled.

It has been speculated that minimally invasive bone cement injection has significant clinical potential for use in the treatment of vertebral body fracture or to stabilize osteoporosis. Bioactive bone cement and other cements can gradually form micro cavities from the outside to the inside after the cement sets. The use of conventional PMMA bone cement and related derivatives is limited, as these cements are not suitable for use in spinal surgery.

SUMMARY OF THE INVENTION

The invention is a bioactive bone cement composition including a powder component and a liquid component. The powder component comprises strontium-containing hydroxy apatite, and the liquid component comprises Bisphenol A diglycidylether dimethacrylate resin. These two components are formulated to create a settable fluid substance when mixed together.

The bioactive bone cement can alternatively be in the form of a two paste component system in which the first paste component is comprised of strontium-containing hydroxy apatite, Bisphenol A diglycidylether dimethacrylate resin and a polymerization initiator, and the second paste component is comprised of strontium-containing hydroxy apatite, Bisphenol A diglycidylether dimethacrylate resin, and a polymerization accelerator. The first and second pastes are formulated to create a settable paste substance when mixed together.

DETAILED DESCRIPTION OF THE INVENTION

The invention is a bioactive bone cement that quickly hardens, and chemically bonds, to affix an artificial biomaterial (e.g., implant material). This cement displays in vivo bioactivity, maintains mechanical strength, has adequate stiffness and modulus (compared with other bioactive cements), and improves bone mass through its physical and chemical effects.

The bioactive bone cement of the present invention comprises a powder and liquid component. The powder component is inorganic filler that is comprised of strontium-containing hydroxy apatite (Sr—HA). The liquid component comprises Bisphenol A Diglycidylether Dimethyacrylate (D-GMA) resin. The ratio of liquid component to powder component in the bone cement is in the range of about 30:70 to about 80:20 by weight.

In one embodiment, the bioactive bone cement is provided in a powder-liquid phase, comprising a powder phase material and a liquid phase material. In a second embodiment, the bioactive bone cement is provided in a paste-paste phase, comprising two separate paste materials.

A bioactive bone cement in accordance with the invention is made as follows. The Sr—HA powder is made through a precipitation process (wet method). The process may be suitable for mass production of small crystalline or non-crystalline HA powder. The theoretical value of (Ca+Sr)/p in Sr—HA is 1.67. The initial mixing ratio of Sr/(Sr+Ca) is from about 10 to 100% mol. The Sr/(Sr+Ca) molar ratio in the as-prepared Sr—HA is from about 10 to 100% mol. $H_3PO_4$ was added dropwise to a basic suspension containing $Ca(OH)_2$ and $Sr(OH)_2$ while stirring the suspension at 20° C. The reaction mixture is stirred for a few days and is controlled through pH measurement of the slurry. The slurry was filtered and the product was dried. An alumina ball mill was then used to pulverize the granular product into a fine powder. The resulting pulverized product was under 200 mesh and was then calcined in a high-temperature muffle furnace. Design of the material emphasized bioactivity rather than crystallinity. It is generally expected that the higher crystallinity of the Sr—HA of this invention gives rise to a somewhat slower bioactivity. To maintain the bioactivity of the Sr—HA, while also maintaining crystallinity, the Sr—HA was calcined at 800° C. instead of at 1200° C. (most preferred for maintaining bioactivity while maintaining crystalline potential). In general, bioactivity of the implant material is correlated with the element dissolution and exchange in the implant surface. The final products can be verified using FTIR and X-Ray Diffraction pattern.

To enhance the combination between the powder and the resin, the following steps have been performed. The Sr—HA powder was preferably treated with a coupling agent such as 3-methacryloxypropyl trimethoxy silane, 3-amino ethyl aminopropyl trimethoxy silane, or 3-glycidoxy, propyl trimethoxy silane. Hexamethyl disilazane and derivatives thereof may also be used as a coupling agent to treat the Sr—HA powder in a reflux device. This is a conventional treatment and usually 1% alcohol solution is used as a coupling agent. Benzoyl peroxide (BPO) was added as a polymerization initiator at a ratio between about 0.01 to about 1.5% per unit weight of the treated powder. In an alternative embodiment, benzoyl peroxide may be omitted, and the polymerization reaction in the resulting bioactive cement may be activated by an increase in temperature, such as by immersing a filled and packed mold into water, and raising the temperature of the water. After adding about 1 to about 20% surface treated fumed silica with respect to the total amount of powder component, the powder component was ready.

A Bisphenol A diglycidylether dimethacrylate (D-GMA) resin used as the liquid component of the bioactive bone cement was prepared from approximately about equal weights of D-GMA and Triethylene-glycol dimethacrylate (TEGDMA). Commonly used monomers and additives in bone cements, such as Ethylene-glycol dimethacrylate (EGDMA) or Methyl methacrylate (MMA), may be utilized to modulate the cement modulus and rigidity of the liquid component. In particular, Poly(ethylene glycol) methacrylate (PEGMA), or similar oligomers, may be added within a range of about 1 to about 10 weight % to modulate the cement modulus and rigidity. Commonly utilized polymerization accelerators may be used, such as N,N-Dimethyl-p-toluidine (DMPT), etc., within a range of about 0.05 to about 1.5 weight % with respect to the amount of the liquid components. More preferably, N,N-Dihydroxypropyl-p-toluidine (DHPPT) is used as the polymerization accelerator instead of N,N-Dimethyl-p-toluidine (DMPT), and can be dissolved in the above mixture. The N,N-Dihydroxypropyl-p-toluidine was used as a kind of polymerization accelerator or promoter to react with the polymerization initiator, or starter, to harden the cement.

Bioactive bone cement, and other cements, can gradually form micro cavities from the outside to the inside after the cement sets. The porosity of the cement and the size of the cavities can be controlled and modulated by the size and kind of salt powder. Neutralized Sodium chloride (NaCl in powder form) can be added into the powder component to confer porosity to the cured cement. Alternatively, FDA approved medical agents that are capable of being dissolved in physiological body fluids [such as Poly (N-vinyl-pyrrolidine) (PNVP) mixed together with the powder component of the cement or added into the paste of the cement] can be added to confer potential porosity to the cured cement. The bioactive bone cements may also be mixed with biological substances, such as bone morphogenetic protein (BMP), peptides and growth factors for medical use.

A bioactive bone cement according to the present invention may be supplied in a powder-liquid phase (comprising a powder phase and a liquid phase) or a two-paste phase (comprising two paste phase materials). In the powder-liquid phase, the powder phase material includes surface-treated Sr—HA powder and fumed silica, and the polymerization initiator, whereas the liquid phase includes the resins and a polymerization accelerator. In the two-paste phase, one paste includes powders, the resins, and the polymerization initiator, whereas the other paste includes powders, the resins and the polymerization accelerator. In use, the user either mixes the powder phase material with the liquid phase material, or mixes the two paste materials together. The two-paste phase is generally preferable when there is a large amount of the powder component because kneading the liquid component into the powder component becomes increasingly difficult with increasing quantities of the powder component.

The resulting bioactive bone cement can be used in a conventional manner or through injection via a syringe. The bioactive bone cement of the present invention is particularly suited for use in spinal surgery via injection with a syringe. Syringe injection provides a minimally invasive delivery technique via the use of a syringe and a large bore needle. It also allows the cement to conform precisely to its area of placement. The bioactive bone cement of the present invention is also particularly suited for use as a bone cement because it is fast-setting and has adequate stiffness. These characteristics result in immediate load bearing strength and a stiffness more closely resembling natural bone than either metal or pure ceramic. Bioinductive and bioconductive properties of the bioactive bone cement make it possible to integrate with the bone at the interface, thereby enhancing bone strength. The bioactive bone cement can also be used as a carrier for osteoinductive drugs. It also has its own chemical effects on improving osteoporosis. The osteoporosic effect is enhanced and strengthened by combining the bioactive bone cement with bone metabolism-related peptides, such as human calcitonin analogs (mHCTs) or osteogenic growth peptide (OGP)-mhCTs hybrid. In addition, the low setting temperature exhibited by the bioactive bone cement allows for improved safety by reducing the risk of thermal damage to surrounding tissues during placement of the cement. The bioactive bone cement also exhibits radio-opacity, thus allowing for easy radiographic imaging during surgery which helps to more accurately control cement location and depth. There is no need to add another X-ray opacifier to the bioactive bone cement. The setting time of the SrHA bone cement can be controlled from 5 to 20 minutes and peak curing temperature is under 50° C. After a series of in vitro spinal injection tests, fatigue stiffness of the new injectable bioactive bone cement is close to that of natural bone.

In addition, the developing bioactive bone cement has physical effects on the prophylactic stabilization of osteoporotic vertebral bodies at risk for fracture via its penetration into, and bonding with, cancellous bone, as well as chemical effects on improving osteoporosis due to the existence of certain amounts of strontium in the implant interface and local area. The bioactive bone cement can also be injected and shaped in dense form, gradually producing cavities from the outside to the inside of the cured cement which allows the surrounding bone tissue or osteoblasts to easily grow into the body of the cement.

The bioactive cement of the invention may be injected into the vertebral body for treatment of spinal fractures, injected into long bone or flat bone fractures to augment the fracture repair or to stabilize the fractured fragments, or injected into intact osteoporotic bones to improve bone strength. It is also useful in the augmentation of a bone-screw or bone-implant interface. It is further useful in the carriage and delivery of drugs, including antibiotics, bone inducing agents, cytotoxic agents, and the carriage and delivery of cells to bone (e.g., cells used for gene therapy and cells normally found in the bone marrow). Additionally, it is useful as bone filler in areas of the skeleton where bone may be deficient. Examples of situations where such deficiencies may exist include post-trauma with segmental bone loss, post-bone tumor surgery where bone has been excised, and after total joint arthroplasty. It is further useful as a cement to hold and fix artificial joint components in patients undergoing joint arthroplasty, as a strut to stabilize the anterior column of the spine after excision surgery, and as a bone graft substitute in spinal fusions.

EXAMPLE 1

Sr—HA Powder

Sr—HA powder was made through the precipitation process (wet method) that is particularly suited for mass production of small crystalline or non-crystalline HA-powder. Without being bound by theory, the chemical formula for the process is believed to be as follows:

$$10\ Sr(OH)_2 + 6\ H_3PO_4 \rightarrow Sr_{10}(PO_4)_6(OH)_2 + 18\ H_2O\ \ 10\ Ca(OH)_2 + 6\ H_3PO_4 \rightarrow Ca_{10}(PO_4)_6 + 18\ H_2O$$

The theoretical value of (Ca+Sr)/p in Sr—HA is 1.67. The initial mixing ratio of Sr/(Sr+Ca) is 10% mol. 0.3 moles $H_3PO_4$ were added dropwise to a basic suspension containing 0.45 moles $Ca(OH)_2$ and 0.05 moles $Sr(OH)_2$ in 1000 ml of re-distilled water while being stirred at 20° C. The reaction mixture was stirred for 3 days and pH was controlled through pH measurement of the slurry. In this study, the pH value was maintained at 9.5 for three days before $H_3PO_4$ addition was stopped. The slurry was filtered through a 200-mesh filter and the product was dried at 110° C. An alumina ball mill was then used to pulverize the granular product into a fine powder. The product smaller than 200-mesh was then calcined in a high-temperature muffle furnace at 800° C. for 3 hours.

Figure 1:
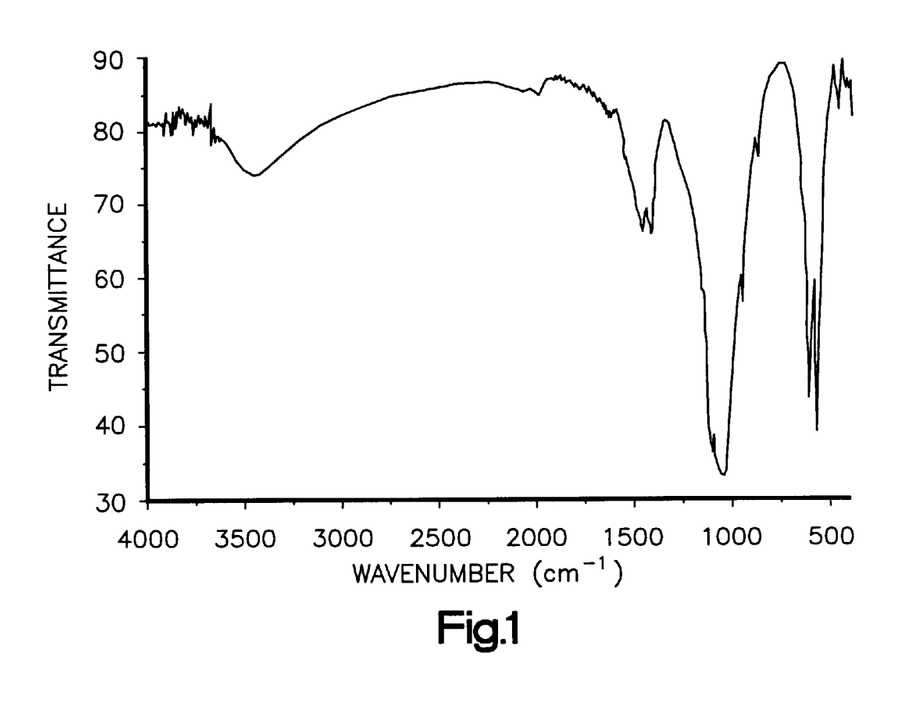
FIG. 1 is a graph showing a Fourier transform infrared spectrum of strontium-containing hydroxy apatite (Sr—HA) powder.
Figure 2:
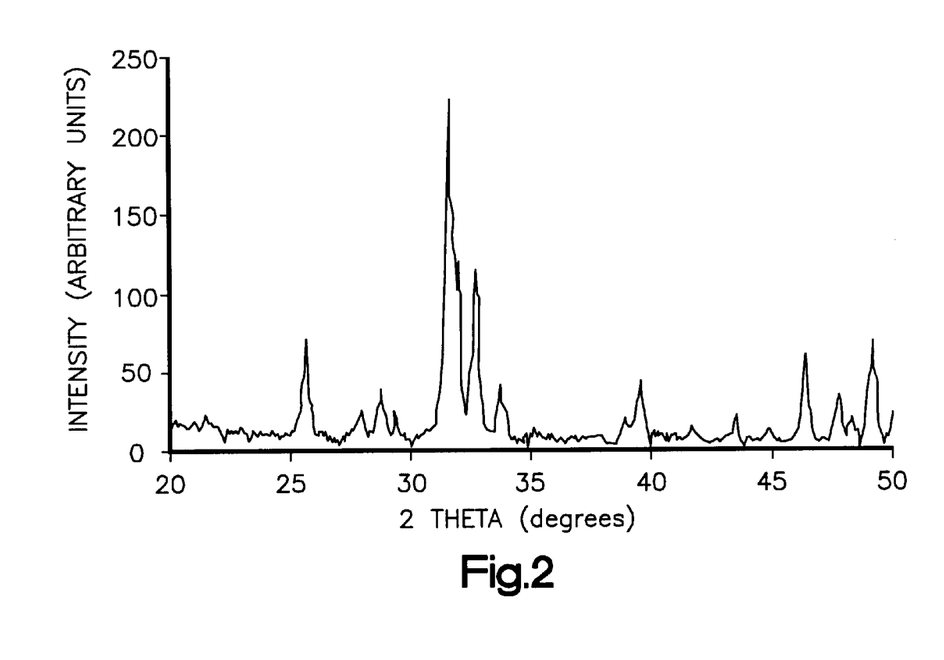
FIG. 2 is a graph showing an X-ray diffraction pattern of strontium-containing hydroxy apatite (Sr—HA) powder.

Fourier Transform InfraRed (FTIR) spectra and X-ray diffraction patterns were obtained to verify the composition and structure of the Sr—HA powders. FTIR results are shown in FIG. 1. Compared with the standard infrared spectra of HA, it shows Sr—HA was typically made through the wet method. The spectra of Sr—HA powder and that of standard HA were found very similar. Three peaks (1097, 1030, 959 $cm^{-1}$) identified phosphate 3 and 1 bands while the 4 band was distinguished by two peaks (604 and 564 $cm^{-1}$). A carbonate 3 band was also observed as peaks (1458 and 1418 $cm^{-1}$), and a carbonate 2 band as a single peak (874 $cm^{-1}$). X-ray diffraction patterns of Sr—HA powder are presented in FIG. 2. The two strong characteristics peaks of HA were shown from the Sr—HA powder made in this invention. The patterns of Sr—HA were very similar to HA, with no detectable secondary phases (for example, tricalcium phosphate (TCP) or calcium oxide (CaO)). The strontium substitution did not appear to affect the diffraction pattern of HA.

EXAMPLE 2

Surface Treatment of Sr—HA Powder

Dry Sr—HA fine powder, about 200-mesh, was treated by stirring with hexamethyl disilazane in a reflux device. It was then dried so that any remains of the treating agent beyond 100° C. would evaporate.

EXAMPLE 3

Preparation of the Resins

D-GMA resin was prepared from approximately equal weights of D-GMA and triethylene-glycol dimethacrylate (TEGDMA). PEGMA was dissolved in the mixture within a range of 0 to about 10 weight % with respect to the amount of liquid component. To increase the homogeneity of the components, the resulting resin was mixed with a magnetic stirrer for 5 hours. Mixing was done at room temperature (20±2° C.) under a dark hood.

EXAMPLE 4

Powder-Resin Restorative (Conventional Use)

A resin blend is prepared from:

| Ingredient | Parts by Weight |
| --- | --- |
| Bisphenol A Diglycidylether Dimethacrylate (D-GMA) | 50 |
| Triethylene-glycol dimethacrylate (TEGDMA) | 45 |
| Poly(ethylene glycol) methacrylate | 4.5 |
| N,N-Dihydroxypropyl-p-toluidine | 0.5 |

A filler blend is prepared from:

| Ingredient | Parts by Weight |
| --- | --- |
| Strontium-containing hydroxyapatite | 95 |
| Fumed silica | 4.5 |
| Benzoyl peroxide | 0.5 |

The resin blend is blended with the filler blend in a ratio of 40:60 weight percent. When blended together, the resulting composite has a working time of about 5 to 8 minutes at room temperature (approximately 25° C.).

EXAMPLE 5

Powder-Resin Restorative (for Injection)

A resin blend is prepared from:

| Ingredient | Parts by Weight |
| --- | --- |
| Bisphenol A Diglycidylether Dimethacrylate (D-GMA) | 50 |
| Triethylene-glycol dimethacrylate (TEGDMA) | 47 |
| Poly(ethylene glycol) methacrylate | 2.75 |
| N,N-Dihydroxypropyl-p-toluidine | 0.25 |

A filler blend is prepared from:

| Ingredient | Parts by Weight |
| --- | --- |
| Strontium-containing hydroxyapatite | 95 |
| Fumed silica | 4.5 |
| Benzoyl peroxide | 0.5 |

Strontium-containing hydroxy apatite cement (SrHAC) specimens were prepared by mixing the 45 wt % surface treated Sr—HA powder and silica into 55 wt % resin, stirring for 2 to 3 minutes and then pouring into a 10 milliliter (ml) disposable syringe with the piston off. The piston was then reinserted and the mixture was injected into a cylindrical Teflon mold [30 millimeter (mm) inner bore, 30 mm deep]. A needle thermometer was inserted into the center of the mold, and the temperature was measured at 1-minute intervals. Setting time was defined as the period between the start of mixing and the time when the temperature had reached midway from the ambient (20° C.) to peak temperatures.

Ten pig spine specimens (T10-L1) were used to test the biochemical stability of the cement. The age at time of death was 10 months. Specimens were harvested, cleaned of soft tissue, frozen and stored below −30° C. Specimen "quality" was inspected visually and radiographically, and those with excessive abnormal anatomic variations were not used in this study. Before use, they were allowed to thaw to room temperature and were cleaned of excess soft tissue, leaving the bony structure, joint capsule and ligaments intact.

Mechanical properties of the intact specimens were recorded using a MTS858 Bionix servo-hydraulic testing machine from MTS Systems Corporation (Eden Prairie, Minn.). Ideally, natural fracture injury should be created on each specimen (by a flexion-compression load). However, in order to create a uniform injury model in all specimens, a pre-injury was created in each specimen. A 2 mm drill bit was used to induce injury on the mid-segment of the body. Specimens were then mounted onto the testing machine and the spinal fixture was used to control the flexion of the spine. Similar mechanical loads as used for the intact specimens were applied. After 10 flexion, compressive loading was performed until a fracture was created in the body of the spine. Mechanical data of injured specimens was then recorded. Bioactive bone cement was injected into the fractured site, and the specimens underwent the same mechanical testing after one hour. A fatigue cycle loading ranging from −100 to −1000 Newtons (N) was then conducted at 1 Hz up to 3,000 cycles. Following cyclic loading, mechanical data was recorded again for each specimen under the same loading conditions of intact testing. Specimens were then loaded to failure after fatigue testing and their strength recorded.

A least-squares linear regression method was used to determine the slope over the range, and all collected data was pooled for statistical analysis with significance defined at $p<0.05$. Analysis of covariance (ANOVA) was used in this study.

All of the specimens were radiographed after fracture, as well as after cement injection and fatigue tests. Location and degree of vertebral bodies filled with SrHAC cement were noted qualitatively. Reconstructed vertebral bodies were then sectioned in either transverse or sagittal planes for qualitative evaluation of the degree of fracture fitting.

Figure 3:
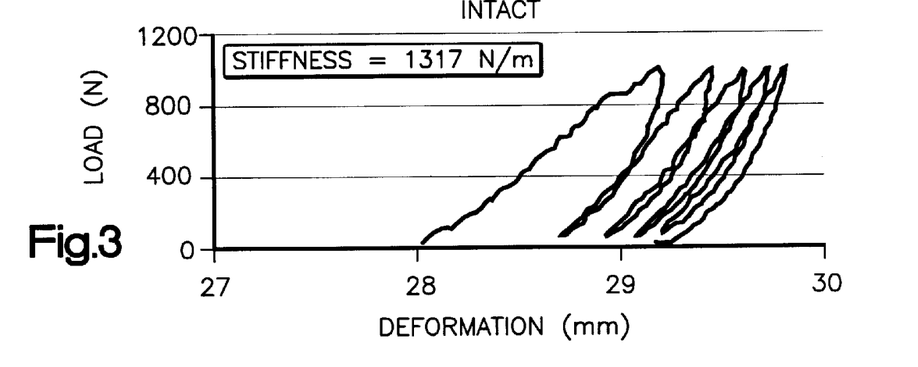
FIG. 3 is a graph showing mean spinal stiffness in an intact spine.
Figure 4:
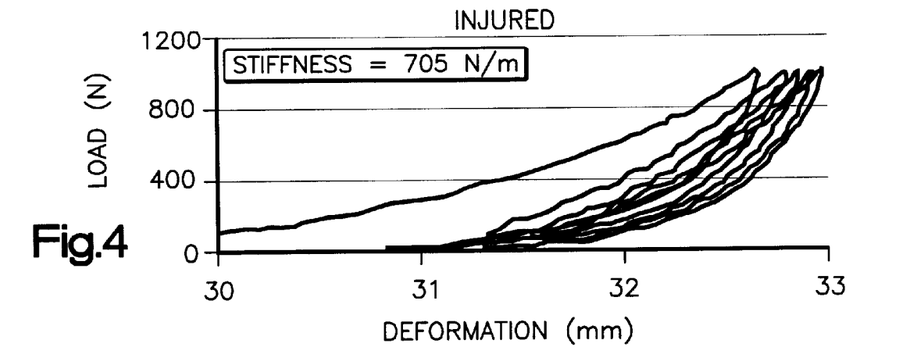
FIG. 4 is a graph showing mean spinal stiffness in a fractured spine.
Figure 5:
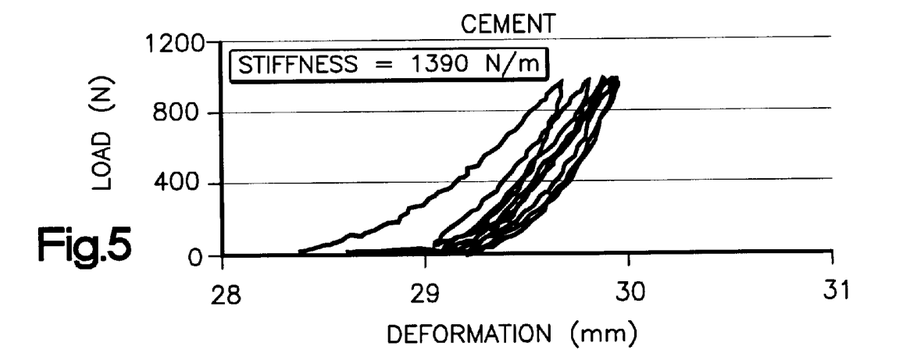
FIG. 5 is a graph showing mean spinal stiffness in a fractured spine after bone cement injection.

Mean spinal stiffness was measured under intact, fractured and bone-cemented conditions. The results are listed in Table 1. After inducing the fracture, the stiffness of the spine dropped significantly (53.3% of intact condition; FIGS. 3 and 4). It was 112% of the initial stiffness (intact condition, $p<0.01$) after bone cement injection (FIG. 5). Stiffness after fatigue loading reduced slightly (95%), suggesting that the bone cement stabilized the collapsed spine. Average failure strength of the spine after fatigue loading was 5056 N.

Figure 6A:
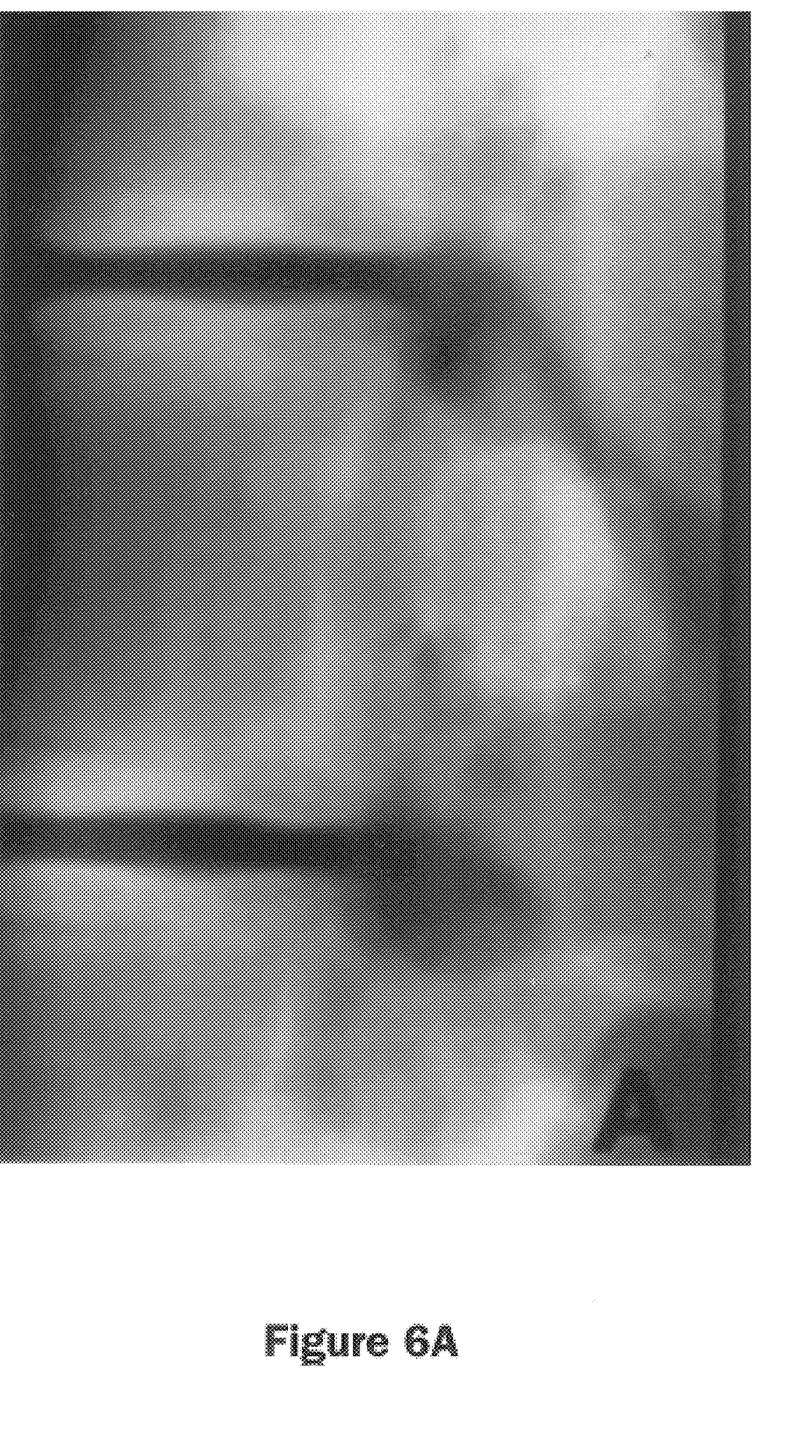
FIG. 6A is a radiograph of an intact spine specimen.
Figure 6B:
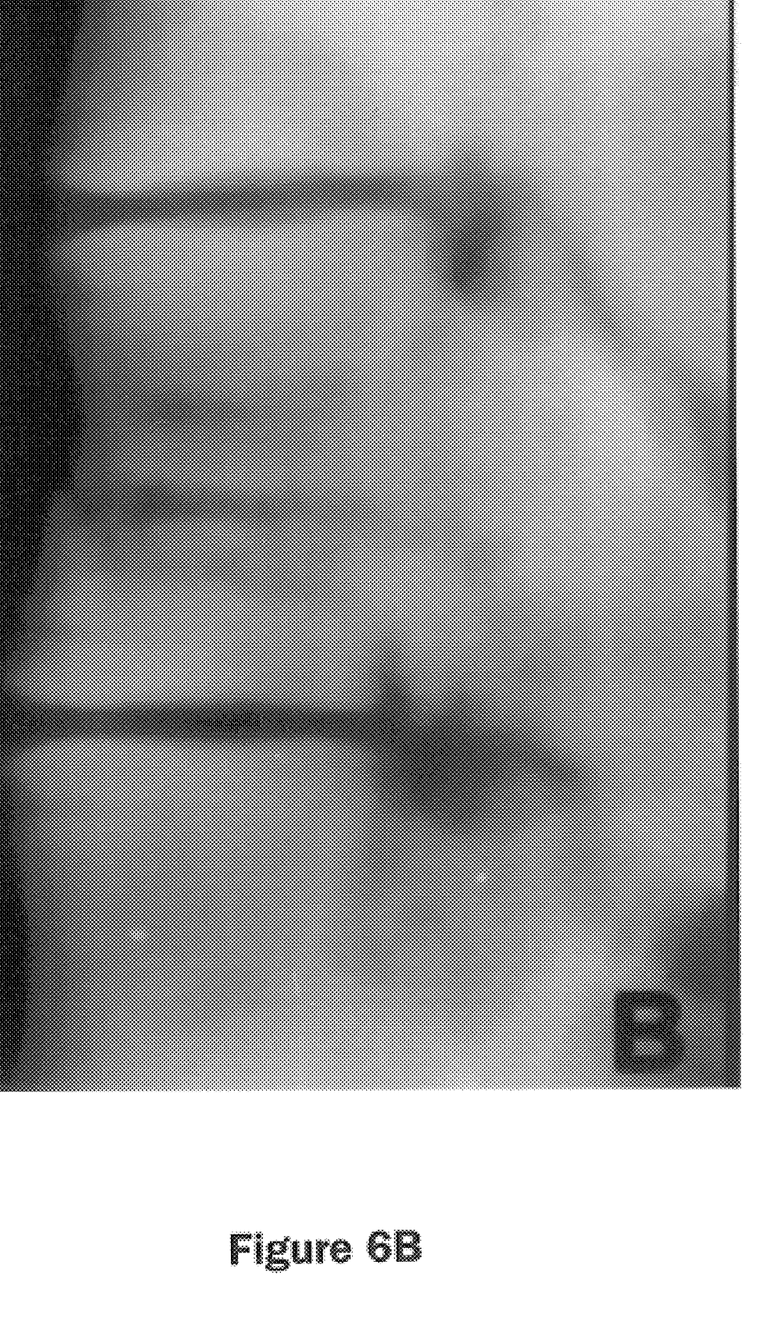
FIG. 6B is a radiograph of a fractured spine specimen.
Figure 6C:
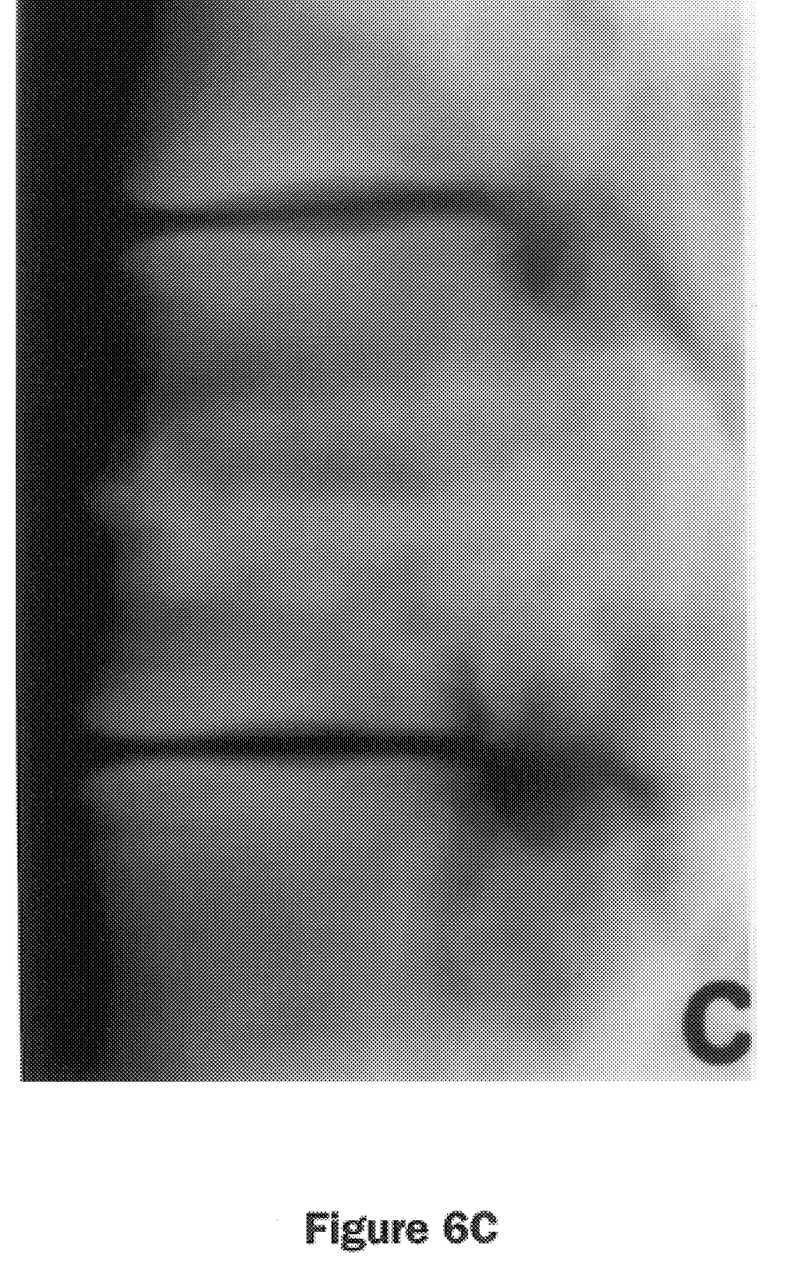
FIG. 6C is a radiograph of a bone-cemented spine specimen taken after fatigue testing.
Figure 7A:
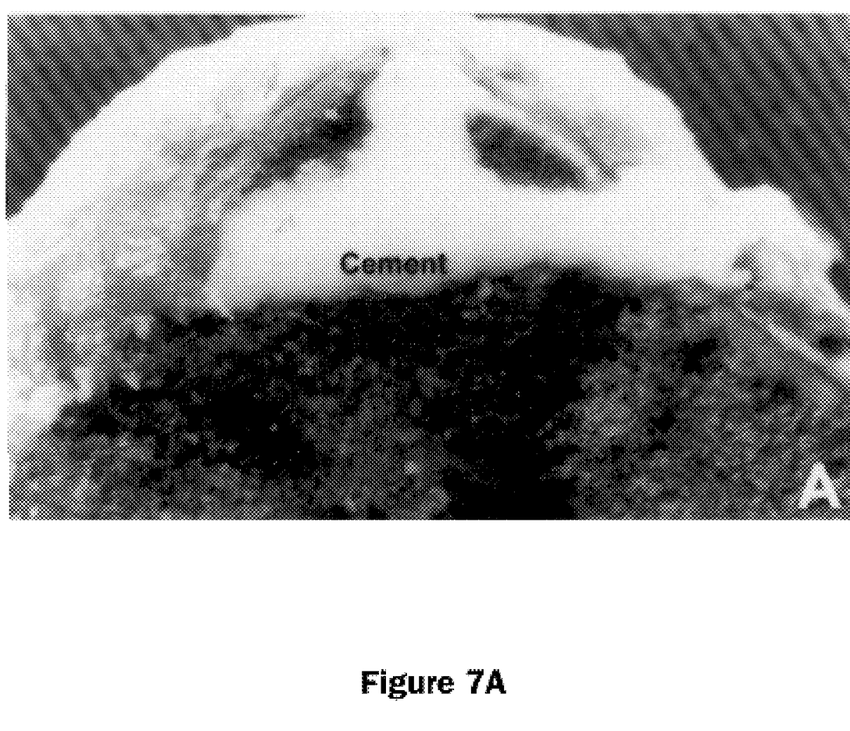
FIG. 7A is a photograph of a transverse section view through a vertebral body filled with SrHA bioactive bone cement after fatigue loading.
Figure 7B:
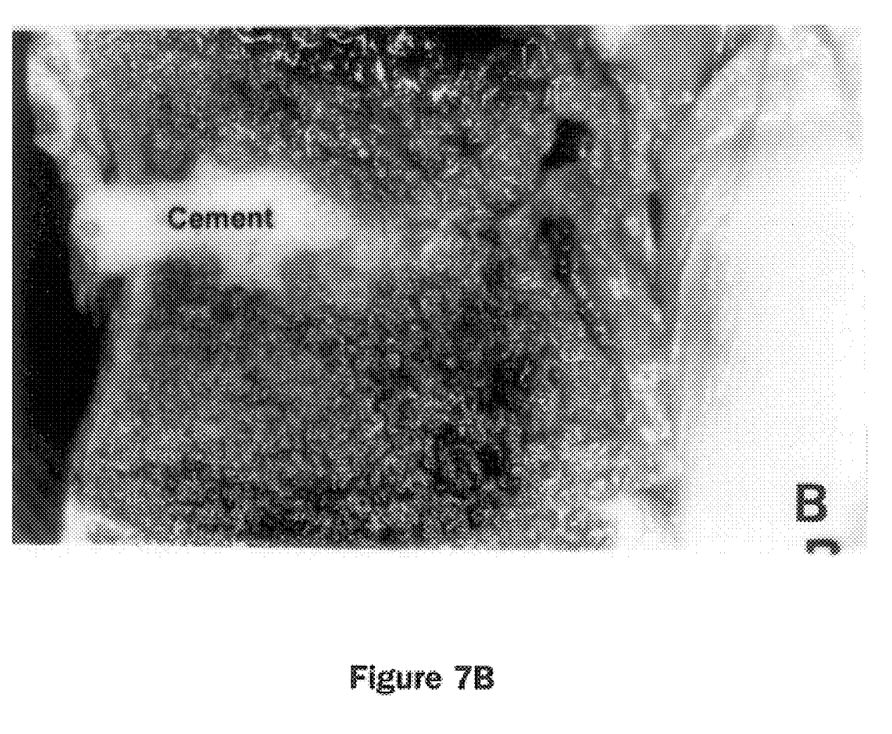
FIG. 7B is a photograph of a sagittal plane view through a vertebral body filled with SrHA bioactive bone cement after fatigue loading.

Morphologic analysis included a review of the radiographs obtained before and after introduction of the SrHAC into the fractured vertebral body. The radiographs showed a nearly complete restoration of vertebral body dimensions (FIGS. 6A, 6B and 6C). Note the complete filling of the gaps in the fracture site in FIG. 6C. There was no evidence of bioactive bone cement retropulsion into the canal of any of the specimens. On review of the cross sections (FIGS. 7A and 7B), there was cement interdigitation into the fracture site and into the cancellous bone of the vertebral body in all specimens.

TABLE 1

Mean spinal stiffness and strength in various conditions

| Condition | Intact (N/mm) | Fractured (N/mm) | Bone-cemented (N/mm) | After fatigue loading | Failure Strength (N) |
|---|---|---|---|---|---|
| Stiffness (Mean ± SD) | 1304.3 ± 145.8 | 694.6 ± 90.2 | 1462.4 ± 154 | 1247.3 ± 130.6 | 5055.8 ± 682 |
| % intact bone | 100 | 53.3 | 112.1 | 95.6 | n/a |

EXAMPLE 6
Paste-Paste Restorative (for Injection)

A first resin formulation is prepared from the following components:

| Ingredient | Parts by Weight |
|---|---|
| Bisphenol A Diglycidylether Dimethacyrlate (D-DMA) | 50 |
| Triethylene-glycol dimethacrylate (TEGDMA) | 47 |
| Poly(ethylene glycol) methacrylate | 2.75 |
| N,N-Dihydroxypropyl-p-toluidine | 0.25 |

An inorganic filler blend is prepared from the following components:

| Ingredient | Parts by Weight |
|---|---|
| Strontium-containing hydroxy apatite | 95 |
| Fumed silica | 5 |

A first paste is prepared from 45% of the inorganic filler blend and 55% of the foregoing resin formulation.

A second resin composition is prepared from the following components:

| Ingredient | Parts by Weight |
|---|---|
| Bisphenol A Diglycidylether Dimethacrylate (D-DMA) | 50 |
| Triethylene-glycol dimethacrylate (TEGDMA) | 47 |
| Poly(ethylene glycol) methacrylate | 3 |
| benzoyl peroxide (BPO) | 0.25 |

The second resin composition is blended with the inorganic filler blend of this example in a ratio by weight of 45:55. The resulting composition forms a second paste capable of catalyzing a hardening reaction. When the two pastes are blended together, the composite has a working time of about 15 to 18 minutes at room temperature.

EXAMPLE 7
Use as an Implant Material Through Preliminary Setting of the Cement (Cold-cure Type)

A resin blend is prepared from the following components:

| Ingredient | Parts by Weight |
|---|---|
| Bisphenol A Diglycidylether Dimethacrylate (D-DMA) | 50 |
| Triethylene-glycol dimethacrylate (TEGDMA) | 45 |
| Poly(ethylene glycol) methacrylate | 4.5 |
| N,N-Dihydroxypropyl-p-toluidine | 0.5 |

An filler blend is prepared from the following components:

| Ingredient | Parts by Weight |
|---|---|
| Strontium-containing hydroxy apatite | 95 |
| Fumed silica | 5 |

In accordance with known dental laboratory techniques, a wax model with the desired shape is prepared. The wax model is then put into an unsetting plaster within a dental flask. After setting of the plaster, the wax is melted and flushed away from the open mold with boiling water. The mixture of the foregoing two components (i.e. resin component to filler component, 40:60 by weight) is prepared and filled into the impression in the plaster mold. After setting of the bioactive bone cement, the plaster mold is broken, and the desired shape of the solid cement is obtained. In this case, if the shape of the desired biomaterial article is conducive to the technique, a metal mold could be prepared and directly filled with the mixture of cement.

EXAMPLE 8
Use as an Implant Material Through Preliminary Setting of the Cement (Heat-cure Type)

A resin blend is prepared from the following components:

| Ingredient | Parts by Weight |
|---|---|
| Bisphenol A Diglycidylether Dimethacyrlate (D-DMA) | 50 |
| Triethylene-glycol dimethacrylate (TEGDMA) | 45 |
| Poly(ethylene glycol) methacrylate | 5 |

An filler blend is prepared from the following components:

| Ingredient | Parts by Weight |
|---|---|
| Strontium-containing hydroxy apatite | 95 |
| Fumed silica | 5 |

In accordance with known dental laboratory techniques, a wax model with the desired shape is prepared. It is then put into an unsetting plaster within a dental flask. After setting of the plaster, the wax is melted and flushed away from the open mold with boiling water. The mixture of the foregoing two components (i.e. liquid component:powder component, 40:60 by weight) is prepared and filled into the impression in the plaster mold.

The polymerization reaction is activated by immersing the packed flask in water and raising its temperature. After the bioactive bone cement is set, the plaster mold can be broken, and the desired shape of the solid cement obtained. In this case, a metal mold can be prepared if the implant is not too complicated, and be directly filled with the mixture of cement. An oven may be used to heat them.

Example 5 had additional testing as follows. The exotherm of polymerization was measured by Differential Scanning Calorimetry (DSC) and only increased to 50° C. for a 20 gram (g) sample. Other compositions, not listed in the table above, were measured with comparable values ranging from 44 to 58° C.

Toxicology testing following ISO 10993 and FDA guidelines was conducted on the composite of Example 7. The composite was found to be non-cytotoxic (MTT test, cell relative growth test and FCM test), non-toxic (acute systemic toxicity), non-irritating (intracutaneous reactivity), non-sensitizing (Kligman and guinea pig), and non-pyrogenic.

Although various embodiments of this invention have been shown and described, it should be understood that various modifications and substitutions, as well as rearrangements and combinations of the preceding embodiments, can be made by those skilled in the art, without departing from the spirit and scope of this invention.

What is claimed is:

1. A cement composition comprising:
   a powder component including a strontium phosphate; and
   a liquid component including Bisphenol A diglycidylether dimethacrylate resin;
   said powder and liquid components being formulated to create a settable substance when mixed together; and
   said powder component also including a calcium phosphate, with relative concentrations of said strontium and calcium phosphates yielding a Sr/(Sr+Ca) molar ratio of 10% or greater.

2. A cement composition comprising:
   a powder component including a strontium phosphate; and
   a liquid component including Bisphenol A diglycidylether dimethacrylate resin;
   said powder and liquid components being formulated to create a settable substance when mixed together; and
   said strontium phosphate being calcined.

3. A cement composition comprising:
   a powder component including a strontium phosphate; and
   a liquid component including Bisphenol A diglycidylether dimethacrylate resin;
   said powder and liquid components being formulated to create a settable substance when mixed together; and
   said composition further comprising a therapeutic compound selected from the group consisting of bone morphogenetic proteins, peptides, and growth factors.

4. A cement composition comprising:
   a powder component including a strontium phosphate, and
   a liquid component including Bisphenol A diglycidylether dimethacrylate resin;
   said powder and liquid components being formulated to create a settable substance when mixed together; and
   said strontium phosphate having the molecular formula $Sr_{10}(PO_4)_6(OH)_2$.

5. A cement composition comprising:
   a powder component including a strontium phosphate; and
   a liquid component including Bisphenol A diglycidylether dimethacrylate resin;
   said powder and liquid components being formulated to create a settable substance when mixed together; and
   said composition further comprising poly (ethylene glycol) methacrylate in an amount specified to modulate the rigidity of said bone cement.

6. A cement composition comprising:
   a powder component including a strontium phosphate; and
   a liquid component including Bisphenol A diglycidylether dimethacrylate resin;
   said powder and liquid components being formulated to create a setable substance when mixed together;
   said composition further comprising a chemical agent capable of dissolving in physiological fluids, said chemical agent being included in an amount specified to control and modulate the porosity and size of cavities formed within said bone cement; and
   said chemical agent being a salt.

7. A composition as defined in claim 6 wherein said salt is sodium chloride.

8. A cement composition comprising:
   a powder component including a strontium phosphate; and
   a liquid component including Bisphenol A diglycidylether dimethacrylate resin;
   said powder and liquid components being formulated to create a settable substance when mixed together;
   said composition further comprising a chemical agent capable of dissolving in physiological fluids, said chemical agent being included in an amount specified to control and modulate the porosity and size of cavities formed within said bone cement; and
   said chemical agent being poly(N-vinyl pyrrolidine).

9. A cement composition comprising:
   a powder component including a strontium phosphate; and
   a liquid component including Bisphenol A diglycidylether dimethacrylate resin;
   said powder and liquid components being formulated to create a setable substance when mixed together; and
   said composition further comprising a therapeutic compound selected from the group consisting of bone morphogenetic proteins, peptides, and growth factors, said peptides being bone metabolism-related peptides.

10. A cement composition comprising:
    a powder component including a strontium phosphate; and
    a liquid component including Bisphenol A diglycidylether dimethacrylate resin;
    said powder and liquid components being formulated to create a settable substance when mixed together; and
    said composition further comprising a therapeutic compound selected from the group consisting of bone morphogenetic proteins, peptides, and growth factors, said peptides being selected from the group consisting of human calcitonin analogs, osteogenic growth peptides, and osteogenic growth peptide-human calcitonin analog hybrids.

* * * * *

UNITED STATES PATENT AND TRADEMARK OFFICE
CERTIFICATE OF CORRECTION

PATENT NO.    : 6,593,394 B1
DATED         : July 15, 2003
INVENTOR(S)   : Li et al.

It is certified that error appears in the above-identified patent and that said Letters Patent is hereby corrected as shown below:

Column 11,
Line 56, delete "," and insert -- ; --.

Column 12,
Line 15, delete "setable" and insert -- settable --.
Line 46, delete "setable" and insert -- settable --.

Signed and Sealed this

Sixteenth Day of September, 2003

JAMES E. ROGAN
*Director of the United States Patent and Trademark Office*